United States Patent [19]

Drauz et al.

[11] Patent Number: 5,631,385
[45] Date of Patent: May 20, 1997

[54] METHOD FOR THE PREPARATION OF N-SUBSTITUTED 4-KETOPROLINE DERIVATIVES

[75] Inventors: Karlheinz Drauz; Matthias Kottenhahn, both of Freigericht; Klaus Stingl, Alzenau, all of Germany

[73] Assignee: Degussa Aktiengesellschaft, Frankfurt, Germany

[21] Appl. No.: 671,535

[22] Filed: Jun. 27, 1996

[30] Foreign Application Priority Data

Jul. 4, 1995 [DE] Germany .................. 195 24 339.0

[51] Int. Cl.$^6$ ............................................... C07D 207/46
[52] U.S. Cl. ........................ 548/530; 548/533; 548/537; 548/538; 548/540
[58] Field of Search ...................... 548/530, 533, 548/537, 538, 540

[56] References Cited

U.S. PATENT DOCUMENTS 5,136,101  8/1992  Fried ............................ 568/402

*Primary Examiner*—Johann Richter
*Assistant Examiner*—Jane C. Oswecki
*Attorney, Agent, or Firm*—Cushman Darby & Cushman, IP Group of Pillsbury Madison & Sutro, LLP

[57] ABSTRACT

Method for the preparation of N-protected 4-ketoproline derivatives of formula I

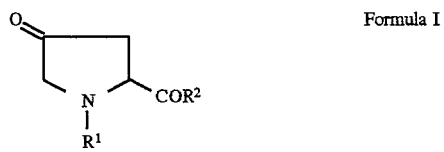

Formula I by oxidation of the corresponding N-protected 4-hydroxyproline derivatives of

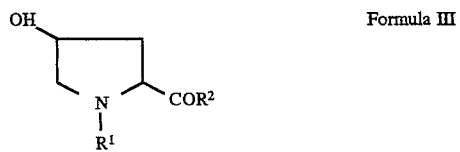

Formula III using the system TEMPO (2,2,6,6-tetramethylpiperidinyl oxy free radical)/NaOCl.

8 Claims, No Drawings

METHOD FOR THE PREPARATION OF N-SUBSTITUTED 4-KETOPROLINE DERIVATIVES

BACKGROUND INFORMATION

The invention relates to a new method for the preparation of N-protected 4-ketoproline derivatives.

N-protected 4-ketoproline derivatives of the general formula I are inter alia important starting compounds for the preparation of the ACE angiotensin-converting enzyme, inhibitor Spirapril [7-(N-(1-(S)-carbethoxy-3-phenylpropyl)-(S)-alanyl-1,4-dithia-7-azaspiro(4,4)nonan-8-(S)-carboxylic acid] of formula II, which is used for the treatment of high blood pressure and of cardiovascular disorders (U.S. Pat. No. 4,470,972).

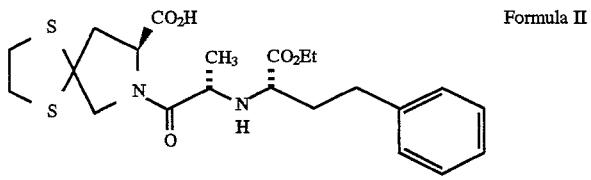

Formula II

Methods for the synthesis of 4-ketoproline derivatives of the general formula I are usually based on oxidizing agents containing heavy metals such as, for example, various chromium-containing oxidising systems (see U.S. Pat. No. 4,296,113) or $RuO_2$/NaOCl (see DD-A5 283 626). These methods have the disadvantage that they require additional safety measures during the carrying out of the reaction, as well as an elaborate and expensive removal of the heavy metals on completion of the reaction.

DD-A5 283 626 describes a method for the preparation of (2S)-N-benzyloxycarbony-4-ketoproline, which method does not involve heavy metals and uses as an oxidizing agent a sulphur trioxide-pyridine complex. This method has the disadvantage that, in using pyridine, one is likewise employing a substance which is very damaging to the environment and highly toxic for humans.

SUMMARY OF THE INVENTION

In the light of these problems, the object of this invention was to provide an environmentally favorable method for the preparation of N-protected 4-ketoproline derivatives of the general formula I, which dispenses with heavy metals and toxic reagents such as pyridine, achieves high product yields and products of high purity and also has economic advantages. This and other objects are fulfilled by a method having the characteristics and properties of the invention described herein. In particular, the invention involves methods for the preparation of N-protected 4-ketoproline derivatives of the general formula I,

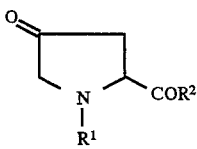

Formula I wherein $R^1$ signifies ($C_1$–$C_6$) alkyl, CO-$R^3$ or fluorenylmethoxycarbonyl, $R^2$ signifies $NH_2$, $OR^4$, $R^3$ signifies (H), ($C_1$–$C_6$) alkyl, phenyl, benzyl, benzyloxy, $NH_2$, $NO_2$-phenyloxy, $NO_2$-benzyloxy, ($C_1$–$C_6$) alkoxy or phenyloxy, $R^4$ signifies ($C_1$–$C_6$) alkyl, benzyl, phenyl, $NO_2$-benzyl, $NO_2$-phenyl or alkyl, whereby the compound of formula I is obtained from the corresponding N-protected 4-hydroxyproline derivatives by oxidation using 2,2,6,6-tetramethylpiperidinyl oxy free radical in the presence of hypochlorite solution. The various narrower embodiments described below provide advantageous procedural modifications, as well as novel substances obtainable as products in the method of the invention.

DETAILED DESCRIPTION OF THE INVENTION

It has now been found that the compounds of the general formula I

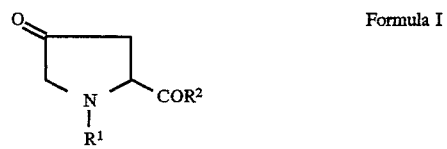

Formula I can be obtained with far greater safety to the environment and more economically, at the same time with high product yields and products of high purity, when the corresponding 4-hydroxy-substituted analogues thereof, possessing the general formula III,

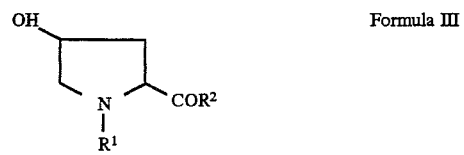

Formula III wherein $R^1$ and $R^2$ have the meanings given above, are converted into the N-protected 4-ketoproline derivatives through oxidation by means of TEMPO 2,2,6,6-tetramethylpiperidinyl oxy free radical, in the presence of a hypochlorite solution such as, for example, NaOCl, or NaOBr generated from NaOCl and KBr.

In the conversion, the quantity of the nitroxy radical (TEMPO) used is in the range of about 0.05 to about 10 mol %, advantageously about 0.5 to about 2 mol %, and the quantity of the hypochlorite solution [NaOCl or NaOBr (generated from NaOCl and KBr), normally about 12 to about 13%] used is from about 1 to about 10 equivalents, advantageously about 1 to about 4 equivalents. Thus, in the method according to the invention, by way of example, hypochlorous or hypobromous acid are generated in situ from technical chlorine bleaching solution or from technical chlorine bleaching solution and KBr by lowering the pH value using acid or a pH-lowering base, advantageously, for example, sodium hydrogen carbonate. The oxidation reaction proceeds at temperatures of from about −20° to about 40° C., particularly advantageously at between about 0° and about 15° C.

All inert organic solvents have in principle proved suitable as additional solvents. Here organic solvents which form a two-phase system with the aqueous solution are particularly preferred. The reaction can also be carried out in a one-phase solvent mixture water/organic solvent. Particularly advantageous, however, are halogenated hydrocarbons such as, for example, dichloromethane, chloroform, 1,1,1-trichloroethane or else esters of formic acid and acetic acid. To remove excess hypochloric acid, the reaction mixture is worked up with a reducing agent such as, for example, sodium thiosulphate solution. On completion of the reaction, in order to separate off the organic phase the pH is adjusted to within a range of about 8 to about 12, advantageously of about 9 to about 10, optionally by means of a base, for example, an inorganic base such as NaOH, NaHCO₃, KOH, or an organic phase, such as NEt₃ or N-methylmorpholine. The pH is then made acid using, for example, an inorganic acid such as HCl or H₂SO₄, and extraction is carried out using an organic solvent which dissolves the product; examples of the latter are toluene, methylene chloride, methyl isobutyl ketone or tert.-butyl methyl ether. After removal of the solvent, the oxidation products of the general formula I are obtained in high purity in the form of oils or solids.

The method according to the invention is shown again below in schematic form:

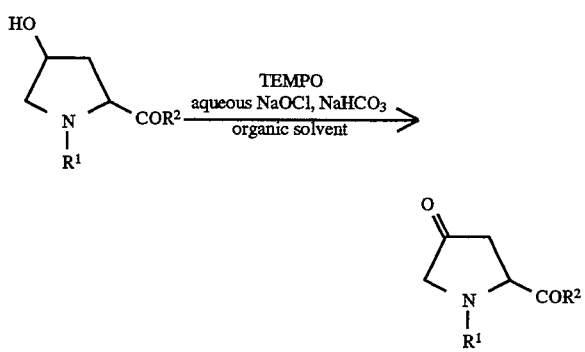

TEMPO=2,2,6,6-tetramethylpiperidinyl oxy free radical

The N-protected hydroxyproline derivatives are known in the technical literature and are obtainable in the manner described in J. Med. Chem. 21,607 (1978).

The method described is illustrated by the examples below, without being limited thereto.

EXAMPLES

General oxidation procedure using the system TEMPO/NaOCl:

A technical NaOCl solution (2 equivalents) adjusted to pH 9.0 by means of sodium hydrogen carbonate is added dropwise at +5° C. to a 10 to 20 wt. % solution of N-protected hydroxyproline methyl ester (1 equivalent) in dichloromethane and 1 mol % of TEMPO in such a way that a temperature of +15° C. is not exceeded. When addition is complete, the reaction mixture is stirred for a further 10 min and the phases are then separated. The aqueous phase is extracted once more with small quantities of dichloromethane and the combined organic extracts are washed once with each of 5% aqueous sodium thiosulphate solution and 5% aqueous sodium hydrogen carbonate solution. After the organic extract has been dried with MgSO₄ and the solvent removed, the resulting product is a yellow oil or solid.

The Examples now given were synthesised as described in the general procedure above.

Example 1

(2S)-N-Boc-4-oxoproline methyl ester 5.9 g (89%) of product is obtained as a light-yellow oil from 6.1 g of (2S,4R)-N-boc-4-hydroxyproline methyl ester. Purity: >95% by ¹H-NMR.

Example 2

(2S)-N-Benzoyl-4-oxoproline methyl ester 5.72 g (93%) of product is obtained as a light-brown oil from 6.23 g of (2S,4R)-N-benzoyl-4-hydroxyproline methyl ester. Purity: ~93% by ¹H-NMR.

Example 3

(2S)-N-Benzyloxycarbonyl-4-oxoproline methyl ester 25.3 g (88%) of product is obtained as a light-yellow oil from 29.0 g of (2S,4R)-N-benzyloxycarbonyl-4-hydroxyproline methyl ester. Purity: 96% by HPLC and ¹H-NMR.

Example 4

(2S)-N-Benzyloxycarbonyl-4-oxoproline ethyl ester 12.5 g (86%) of product is obtained as a yellow oil from 14.6 g of (2S,4R)-N-benzyloxycarbonyl-4-hydroxyproline ethyl ester. Purity: 97% by HPLC.

Example 5

(2S)-N-Benzyloxycarbonyl-4-oxoproline isopropyl ester 9.5 g (89%) of product is obtained as a light brown oil from 10.7 g of (2S,4R)-N-benzyloxycarbonyl-4-hydroxyproline isopropyl ester. Purity: 92% by HPLC.

Example 6

(2S)-N-Benzyloxycarbonyl-4-oxoproline n-butyl ester 13.4 g (84%) of product is obtained as a light brown oil from 16.1 g of (2S,4R)-N-benzyloxycarbonyl-4-hydroxyproline n-butyl ester. Purity: 96% by HPLC.

Example 7

(2S)-N-Benzyloxycarbonyl-4-oxoproline benzyl ester 19.0 g (54%) of product is obtained as a colourless solid having a melting point of 56° C. from 35.3 g of (2S,4R)-N-benzyloxycarbonyl-4-hydroxyproline benzyl ester. Purity: >95% by ¹H-NMR.

Example 8

(2S)-N-Benzoyl-4-oxoproline benzyl ester 13.2 g (82%) of product is obtained as a light-brown oil from 16.2 g of (2S,4R)-N-benzoyl-4-hydroxyproline benzyl ester. Purity: 91% by HPLC.

We claim:

1. A process for the preparation of N-substituted 4-ketoproline derivatives of the general formula I by oxidation of the corresponding N-substituted 4-hydroxyproline derivatives of the general formula III

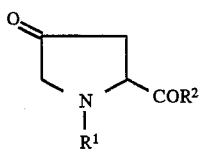
Formula I

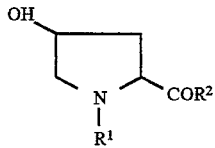
Formula III wherein $R^1$ is ($C_1$–$C_6$) alkyl, CO-$R^3$ or fluorenylmethoxycarbonyl, $R^2$ is $NH_2$, $OR^4$, $R^3$ is (H), ($C_1$–$C_6$) alkyl, phenyl, benzyl, benzyloxy, $NH_2$, NO2-phenyloxy, $NO_2$-benzyloxy, ($C_1$–$C_6$) alkoxy or phenyloxy, and $R^4$ is ($C_1$–$C_6$) alkyl, benzyl, phenyl, $NO_2$-benzyl, $NO_2$-phenyl or alkyl, wherein the reaction is carried out in the presence of 2,2,6,6-tetramethylpiperidinyl oxy free radical (TEMPO) and a hypohalide solution.

2. The process according to claim 1, wherein the hypohalide is NaOCl or NaOBr.

3. The process according to claim 1 or 2, wherein NaOBr is generated from NaOCl by the addition of KBr.

4. The process according to claim 1, wherein the reaction is in a two-phase system comprising an aqueous phase and of an organic phase immiscible therewith.

5. The process according to claim 4, wherein a halogenated solvent is used as solvent for the organic phase.

6. The process according to claim 5, wherein the halogenated solvent is dichloromethane, chloroform, 1,1,1-trichloroethane, an ester of formic acid or an ester of acetic acid.

7. The process according to claim 1, wherein the oxidation reaction is carried out at temperatures of from –20° C. to 40° C.

8. An (2S)-N-benzyloxycarbonyl-4-oxoproline Isopropyl ester or an (2S)-N-benzyloxycarbonyl-4-oxoproline n-butyl ester, which is produced by oxidation of the corresponding N-substituted 4-hydroxyproline derivative compound of the general formula III

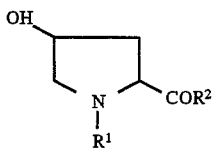
Formula III wherein $R^1$ is ($C_1$–$C_6$) alkyl CO—$R^3$ or fluorenylmethoxycarbonyl, $R^2$ is $NH_2$, $OR^4$, $R^3$ is (H), ($C_1$–$C_6$) alkyl, phenyl, benzyl, benzyloxy, $NH_2$, NO2-phenyloxy, $NO_2$-benzyloxy, ($C_1$–$C_6$) alkoxy or phenyloxy, and $R^4$ is ($C_1$–$C_6$) alkyl, benzyl, phenyl, $NO_2$-benzyl, $NO_2$-phenyl or alkyl, wherein the reaction is carried out in the presence of 2,2,6,6-tetramethylpiperidinyl oxy free radical (TEMPO) and a hypohalide solution.

* * * * *